(12) United States Patent
Weldemariam et al.

(10) Patent No.: US 10,950,355 B2
(45) Date of Patent: Mar. 16, 2021

(54) SIMULATION METHOD AND SYSTEM

(71) Applicant: International Business Machines Corporation, Armonk, NY (US)

(72) Inventors: Komminist Weldemariam, Nairobi (KE); Maja Vukovic, New York, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 236 days.

(21) Appl. No.: 15/926,286

(22) Filed: Mar. 20, 2018

(65) Prior Publication Data
US 2019/0295730 A1 Sep. 26, 2019

(51) Int. Cl.
*G16H 50/50* (2018.01)
*A61B 5/00* (2006.01)
*A61B 5/16* (2006.01)

(52) U.S. Cl.
CPC ............ *G16H 50/50* (2018.01); *A61B 5/165* (2013.01); *A61B 5/6898* (2013.01)

(58) Field of Classification Search
CPC ....... A61B 5/744; A61B 5/6898; A61B 5/165; A61B 5/0022; A61B 5/7275; A61B 5/6896; A61B 5/681; A61B 5/4088; A61B 5/7264; A61B 5/1112; G16H 50/50
See application file for complete search history.

(56) References Cited

U.S. PATENT DOCUMENTS

| | | | |
|---|---|---|---|
| 6,186,145 B1 | 2/2001 | Brown | |
| 9,704,103 B2 | 7/2017 | Suskind et al. | |
| 10,372,892 B2 | 8/2019 | DeBates et al. | |
| 2007/0130813 A1 | 6/2007 | Stacy | |
| 2007/0207698 A1 | 9/2007 | Stanley | |
| 2008/0208016 A1* | 8/2008 | Hughes | G16H 40/67 600/301 |
| 2008/0313025 A1* | 12/2008 | Chowdhury | G06Q 10/0633 705/7.27 |
| 2009/0197678 A1 | 8/2009 | Huang | |
| 2012/0139828 A1* | 6/2012 | Lok | G09B 7/00 345/156 |
| 2012/0237909 A1* | 9/2012 | Stern | G09B 19/00 434/236 |
| 2013/0281798 A1* | 10/2013 | Rau | A61B 5/4884 600/301 |
| 2014/0113263 A1* | 4/2014 | Jarrell | G09B 19/00 434/262 |

(Continued)

OTHER PUBLICATIONS

Nudd, "Samsung Made VR Bedtime Stories for Kids and Parents Who Can't Be Together in Person Live storytelling app places them in the same fantasy", http://www.adweek.com/adfreak/samsung-made-vr-bedtime-stories-kids-and-parents-who-cant-be-togetherperson-171166; May, 2, 2016.

(Continued)

*Primary Examiner* — Nathan Hillery
(74) *Attorney, Agent, or Firm* — Scully, Scott, Murphy & Presser, P.C.; Shimon Benjamin, Esq.

(57) ABSTRACT

A computer device may identify an interaction device that is capable of outputting a simulation representative of an identified aspect of an entity. The computer device may trigger the identified interaction device to output a simulation of the identified aspect.

20 Claims, 7 Drawing Sheets

(56) References Cited

U.S. PATENT DOCUMENTS

| | | |
|---|---|---|
| 2014/0125678 A1 | 5/2014 | Wang et al. |
| 2015/0262429 A1 | 9/2015 | Shuster et al. |
| 2016/0035132 A1* | 2/2016 | Shuster ................ G06T 19/006 345/633 |
| 2016/0225187 A1 | 8/2016 | Knipp et al. |
| 2017/0103336 A1 | 4/2017 | Hunnicutt |
| 2017/0270822 A1* | 9/2017 | Cohen ..................... G09B 7/00 |
| 2018/0053436 A1* | 2/2018 | Schaefgen .............. G09B 7/02 |
| 2018/0089893 A1* | 3/2018 | Kukis ..................... G06F 1/163 |
| 2018/0189802 A1* | 7/2018 | Hammond ......... G06Q 30/0201 |
| 2019/0033914 A1* | 1/2019 | Aimone ............... A61B 5/0022 |
| 2019/0180637 A1* | 6/2019 | Mealer .................... G09B 5/04 |

OTHER PUBLICATIONS

"Virtual Parenting and Virtual Visitation", https://www.ourfamilywizard.com/solutions/virtual-parenting-and-virtual-visitation, last printed Mar. 20, 2018, 1 page.

Robinson et al., "Separation Anxiety in Children", helpguide.org, http://www.helpguide.org/articles/anxiety/separation-anxiety-in-children.htm, Mar. 2018, 9 pages.

Birnbaum et al., "Therapeutic doll play in the treatment of a severely impaired psychiatric inpatient: dramatic clinical improvements with a nontraditional nursing intervention", J Psychococ Nurs Ment Health Serv, May 2015; 53(5):22-7, Abstract; https://www.ncbi.nlm.nih.gov/pubmed/25974922, 2 pages.

\* cited by examiner

SIMULATION METHOD AND SYSTEM

FIELD

The present application relates generally to computers, and computer applications, and more particularly to computer-implemented methods and systems in interactive communication systems.

BACKGROUND

A first entity, such as a child, may experience separation anxiety when placed in an undesirable setting, such as a daycare, and when separated from a second entity, such as a parent. Different levels of separation anxiety may be alleviated by interacting or engaging with different types of reassurance. In some examples, interactive communication systems may be implemented by interaction devices, such as smart devices and electronic toys, to output content to entertain the first entity.

SUMMARY

In some examples, a method for generating a simulacrum representative of an entity is generally described. The method may include determining, by a computer device, a current context associated with a first entity and a second entity. The current context may indicate that the first entity and second entity are separated. The method may further include detecting, by the computer device, that the first entity is experiencing separation anxiety relating to the separation of the first entity and the second entity. The method may further include in response to detecting that the first entity is experiencing separation anxiety, identifying, by the computer device, an aspect of the second entity based on engagement data associated with historical interactions between the first entity and the second entity. The method may further include identifying, by the computer device, an interaction device that is capable of outputting a simulacrum representative of the identified aspect of the second entity. The method may further include triggering, by the computer device, the identified interaction device to output the identified simulacrum.

In some examples, a system effective to generate a simulacrum representative of an entity is generally described. The system may include a memory configured to store a set of instructions. The system may further include a processor configured to be in communication with the memory. The system may further include at least one interaction device configured to be in communication with the processor. The processor may be configured to execute the set of instructions to determine a current context associated with a first entity and a second entity. The current context may indicate that the first entity and second entity are separated. The processor may be further configured to execute the set of instructions to detect that the first entity is experiencing separation anxiety relating to the separation of the first entity and the second entity. The processor may be further configured to execute the set of instructions to in response to the detection that the first entity is experiencing separation anxiety, identify an aspect of the second entity based on engagement data associated with historical interactions between the first entity and the second entity. The processor may be further configured to execute the set of instructions to identify an interaction device among the at least one interaction device, wherein the identified interaction device is capable of outputting a simulacrum representative of the identified aspect of the second entity. The processor may be further configured to execute the set of instructions to trigger the identified interaction device to output the identified simulacrum.

In some examples, a computer program product for generating a simulacrum representative of an entity is generally described. The computer program product may include a computer readable storage medium having program instructions embodied therewith. The program instructions may be executable by a processing element of a device to cause the device to perform one or more methods described herein.

Further features as well as the structure and operation of various embodiments are described in detail below with reference to the accompanying drawings. In the drawings, like reference numbers indicate identical or functionally similar elements.

DETAILED DESCRIPTION

Figure 1:
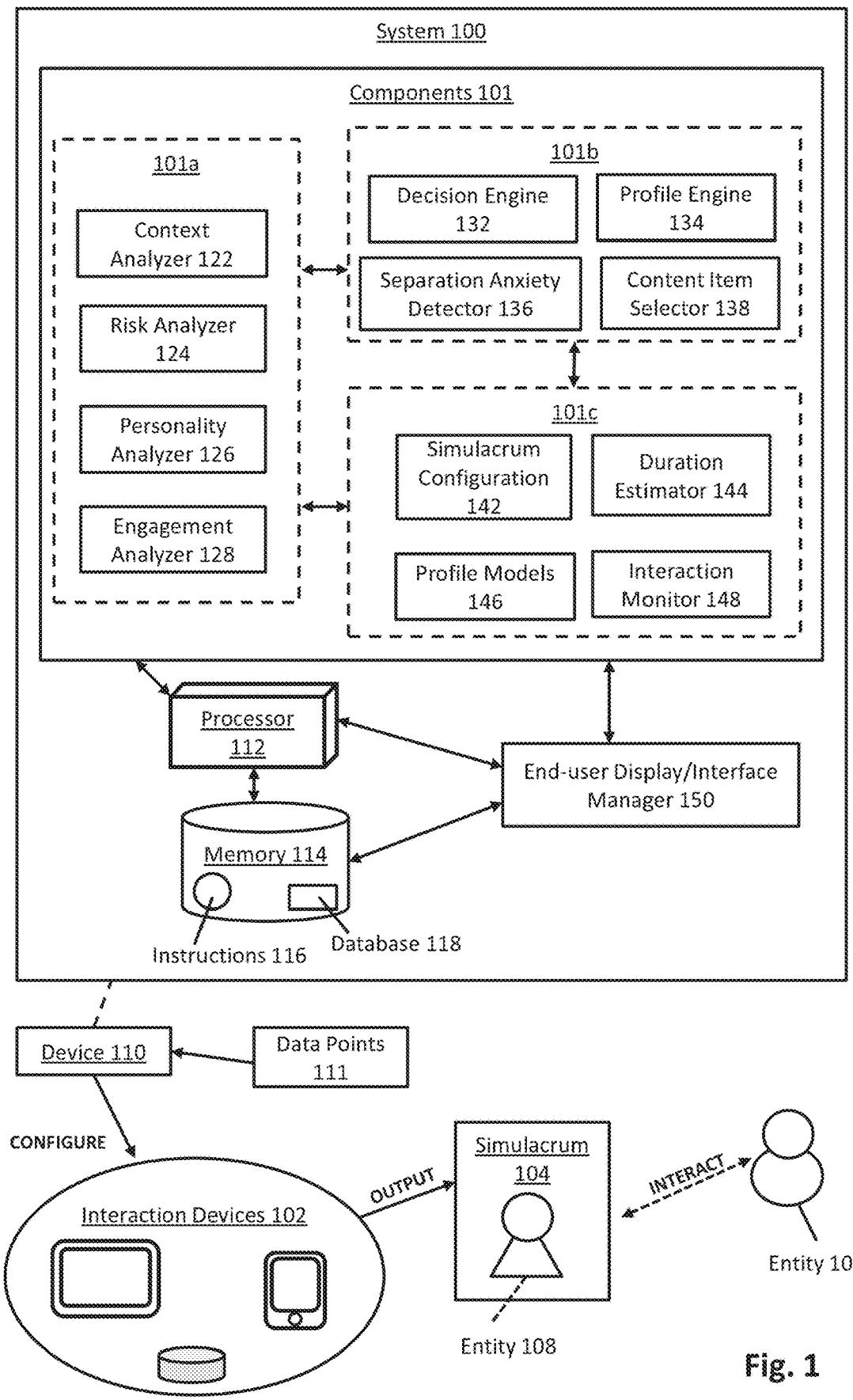
FIG. 1 illustrates an example computer system in one embodiment that can be utilized to implement simulacrum generation based on separation anxiety.

In some examples, methods and systems (e.g., a system 100 shown in FIG. 1, and further described below) for aiding the well-being of a first entity (e.g., a child) by facilitating a virtual interaction with a second entity (e.g., a parent, a caregiver, and/or a sibling), in the form of a simulacrum, and for presenting one or more aspects of the second entity on a user interface of an interaction device, based on context and estimated context related to the first and second entities, are described. The interaction device may be a phone, computer display, doll, augmented-reality glasses, watch, voice vehicle dashboard, and/or another device. The interaction device may display or simulate one or more aspects of the second entity, such as an avatar of the second entity, an image of the second entity, mannerisms of the second entity, voice of the second entity, multimedia, and/or another aspect of second entity.

Some examples of context may include, but not limited to, location of the first entity, setting of the first entity, location of the second entity, setting of the second entity, cognitive state of the first entity, current amount of separation time between the second entity and the first entity, anticipated amount of separation time between the second entity and the first entity, current number and nature of entities (e.g., caregiver or companion) in proximity to the first entity, history of concerns, background of the first entity, cohort related to the first entity (e.g., autism), cohort related to the second entity, and/or other situations related to the first and second entities.

In some examples, the system 100 may decide what to display or simulate by learning the different interactions between the first entity and the second entity to automatically match the current context of the first entity, and generate the simulation or another action (e.g., generate a simulacrum). If desired, the system 100 may create a group setting based on the cohort and context of the first entity. A degree of realism of a simulacrum can be controlled and may be based on said context (e.g., photorealistic or avatar). In some examples, the second entity may configure the system 100 prior to an implementation of the system 100 in order to control the simulacrum to be generated and/or outputted. The degree of realism can be inferred from historical interactions collected and can be displayed or simulated, which can be provided to the second entity for approval. In an example, the system 100, with permission from the second entity, may record what the first entity says, the emotions of the first entity, and/or video of the first entity when the second entity is away from the first entity, where the recorded material may be presented to the second entity in a future time.

Some examples of the generated and/or outputted simulacrum may include representations of a calming action, such as the second entity singing, music, photos of the home, photos of a vacation, recording of the second entity telling a story, entering a virtual reality with the second entity, and/or other aspects of the second entity. In some examples, the generated and/or outputted simulacrum may perform actions such as preparing the first entity for an anticipated absence of the second entity, listening to the first entity speaking, reassuring the first entity, offering choices to the first entity, staying calm in response to negative behavior from the first entity, praising the first entity, and/or other actions.

The system 100 may also be configured to detect possible anxiety triggers. For example, a device, such as a smart speaker, may be used to detect and record audio data, such as sounds, noises, commands, from the first entity who may be experiencing separation anxiety. The system 100 may detect security and privacy concerns and other communication means concerns (e.g., intermittent connectivity, device power, etc). For example, if a level of the detected concern is high (e.g., when the detected data includes privacy concerns, and/or when communication means may be susceptible for possible data leak), the system 100 may encrypt information received at the devices, or may trigger a local (e.g., on-device or offline) artificial intelligent (AI) agent that was trained using a plurality of data (e.g., data about context of the first entity, cohort, and/or past engagement/ interaction history), as an output simulacrum. In some examples, the triggered and/or outputted local artificial intelligence agent may be refrained from communicating or interacting with another device, and may continue to provide the simulacrum service for the first entity until the detected concern is elevated. In some examples, interactions with the outputted simulacrum may be performed on an opt-in basis based on preconfigured instructions.

In some examples, the generated and/or outputted simulacrum may include interactive images of the second entity, and may be displayed on a wrist band that fastens around the wrist of the first entity or another device worn by the first entity. The first entity, e.g., while in daycare or preschool or another location, may take comfort from wearing this wrist band or another device containing a simulacrum of the second entity.

In some examples, the system 100 may be implemented with a personalized transitional item or toy, such as an interactive stuffed animal, to aid in the emotional transitions of the first entity. The interactive toy may have virtual elements related to the second entity, which may be reassuring to the first entity experiencing separation anxiety.

In some examples, the outputted simulacrum may be a representation of the second entity telling a story that may include elements, such as characters and settings provided by the second entity prior to being separated from the first entity. In some examples, a display of the interactive device may be filled with images related to the story and a simulacrum representative of the second entity telling the story may be outputted by the interactive device. The story duration and excitement level may be influenced by the time of day and context. In some cases, objects in the real world may be incorporated into the story.

In some examples, the system 100 may, with permission from the second entity, learn the needs and desires of the first entity, from a plurality of data (e.g., data about context of the first entity, cohort, and/or past engagement/interaction history), in order to determine (e.g., using natural language processing, deep-learning techniques) educational content and display educational or entertaining content (or soothing content) from online sources such as video streaming services.

FIG. 1 illustrates an example computer system 100 that can be utilized to implement simulacrum generation based on separation anxiety, arranged in accordance with at least some embodiments described herein. In some examples, the system 100 may be implemented by a device 110 to facilitate a generating and/or an output of a simulacrum 104 by one or more interaction devices 102, and to facilitate interaction between an entity 106 and the simulacrum 104. In some examples, the device 110 may be a phone, a computer, or a computer device configured to be in communication with one or more interaction devices 102 directly (e.g., via a wire, and/or cable), or wirelessly (e.g., BLUETOOTH, near-field communication, Internet, WI-FI, and/or cellular network). Some examples of interaction devices 102 may include, but not limited to, one or more of a computer display, a doll, a toy, an augmented-reality glasses, a watch, a voice vehicle dashboard, a wearable device, and/or a tablet computer device. In some examples, the device 110 may be an interaction device among the interaction devices 102, such that the device 110 may implement the system 100 to generate and/or output the simulacrum 104. In some examples, the device 110 and one or more of interaction devices 102 may be located within a same vicinity (e.g., a location, a room, a building, and/or a house) or may be located in separate locations (e.g., different rooms, buildings, and/or houses).

As will be described in more detail below, the system 100 may detect separation anxiety being experienced by an entity 106 when the entity 106 is separated from an entity 108. The device 110 may implement the system 100 to identify an aspect of the entity 108 that may alleviate the separation anxiety being experienced by the entity 106. The device 110 may identify one or more of interaction devices 102 that may be capable of outputting simulacrums representative of the identified aspect of the entity 108. The device 110 may further trigger, or configure, the identified interaction device 102, based on the identified aspect, to generate, select, and/or output the simulacrum 104 representative of the identified aspect of the entity 108. Examples of the simulacrum 104 may include, but not limited to, a simulation of an action being performed by the entity 108, an image of the entity 108, a voice recording that includes a voice of the entity 108. In some examples, the device 110 may be configured to generate, select, and/or output the simulacrum 104.

The system 100 may include a plurality of components 101, where each component 101 may be configured to perform respective tasks and/or store respective data. In an example shown in FIG. 1, the components 101 of the system 100 may include a context analyzer 122, a risk analyzer 124, a personality analyzer 126, an engagement analyzer 128, a decision engine 132, a profile engine 134, a separation anxiety detector 136, a content item selector 138, a set of simulacrum configurations 142, a duration estimator 144, a set of profile models 146, an interaction monitor 148, and/or an end-user display/interface manager 150 (herein "interface manager 150").

In an example embodiment, one or more components 101 may be partitioned into one or more groups of components. For example, as shown in FIG. 1, the components 101a may include the context analyzer 122, the risk analyzer 124, the personality analyzer 126, and the engagement analyzer 128, the components 101b may include the decision engine 132, the profile engine 134, the separation anxiety detector 136, and the content item selector 138, and the components 101c may include the simulacrum configurations 142, the duration estimator 144, the profile models 146, and the interaction monitor 148.

The system 100 may further include a processor 112 and a memory 114, where the memory 114 may be configured to store selective (e.g., based on data or instructions relevant and importance) data and instructions associated with an implementation of system 100. The processor 112 may be a central processing unit of the device 110. In some examples, the processor 112 may be configured to control operations of components 101. The components 101 of the system 100 may be configured to be in communication with each other, and may be configured to be in communication with the processor 112 and the memory 114, such that each component 101 may store data in the memory 114 and may retrieve data from the memory 114. In some examples, one or more components 101 of the system 100 may be hardware components such as programmable logic devices, microcontrollers, memory devices, and/or other hardware components, of the processor 112 or the device 110. In some examples, one or more components 101 of the system 100 may be software modules that may be implemented with the processor 112 to perform one or more tasks. In some examples, one or more of components 101 may be packaged as an application that may be controlled and/or executed by the processor 112 of the device 110 in order to implement the system 100. For example, the components 101 may be packaged as a mobile application that may be installed on, and executable by, the device 110.

The memory 114 may be configured to selectively store instructions executable by the processor 112 and the components 101. For example, in one embodiment, the memory 114 may store a set of instructions 116, where the instructions 116 may include instructions, such as executable code, related to noise recognition algorithms, image recognition algorithms, machine learning algorithms, database management algorithms, arithmetic logic, personality determination algorithms, and/or risk analysis algorithms. In some examples, the set of instructions 116 may include explicit instructions and implicit instructions. Examples of explicit instructions may include predefined rules and/or user-supplied rules. Examples of implicit instruction may include inferred rules, using custom designed and trained machine learning models, from historical instructions and interactions data that have demonstrated effective simulacrums. The processor 112 and the components 101 may each be configured to execute one or more portions of the instructions 116 in order to facilitate implementation of the system 100.

The memory 114 may be further configured to store data associated with a database 118, where the database 118 may be a data store including data that may indicate correspondences among a set of simulacrums that represents at least one aspect of the entity 108, and the database 118 may also include a set of anxiety data indicating types and degrees of separation anxiety that may be experienced by the entity 106. The processor 112 and the components 101 may access the database 118, such as performing lookup functions in the database 118, to identify a simulacrum that may reduce a level of anxiety being experienced by the entity 106 (further described below).

The system 100 may learn, with permissions from the second entity, (e.g., custom developed functions and/or models) the interactions of the first entity with other entities. In examples where insufficient data (e.g., historical audio data, image data, from the first entity and/or other entities) are available, the system 100 may apply a heuristic-based learning process, such as storing data representative of reactions from the first entity in response to particular contexts in the database 118 for later comparison. As such, at a subsequent time, reactions from the first entity at a current context may be compared (such as, by the decision engine 132) with the data stored in the database 118 in order to identify a simulacrum to be outputted by one or more interaction devices 102. In examples where sufficient data are available, system 100 may apply one or more machine learning algorithms (which may be a portion of the instructions 116 stored in the memory 114) to learn, or determine, mathematical models that may be used at a subsequent time to monitor and/or predict separation anxiety being experienced by the first entity. In some examples, a plurality of data points 111 (which may be collected by the interaction monitor 148) being used to learn the interactions of the first entity with other entities may include, but not limited to, voice/speech interaction data captured using voice-controlled devices), interaction data captured from user devices (e.g., smart phone, smart speakers), context data, and/or other data collected by the system 100. In some examples, behavioral and emotional aspects of interactions may be learned (such as, by the engagement analyzer 128) from speech audio/recordings using at least one custom trained machine-learning algorithm/model (e.g., Support Vector Machine (SVM), Hidden Markov model (HMM), or deep learning (e.g., Recurrent Neural Networks)). Models (e.g., the profile models 146) learned by the system 100 may be used to detect or predict various behavioral and emotional aspects such as temperament, mood, and/or other emotional aspects. In some examples, custom trained noise detection and face or facial expression detection models, which may be part of the instructions 116, may be used by the system 100, or the separation anxiety detector 136, to detect or predict separation anxiety being experienced by the entity 106. In some examples, the system 100 may learn what may be most soothing for the first entity based on the history of the first entity and other entities in a cohort related to the first entity.

In some examples, each group of components may be configured to perform respective types of tasks. For example, the components 101c may include components that may be configured to interface with devices and/or context outside of the device 110. In an example, the interaction monitor 148 may be configured to detect interactions (such as by controlling sensors configured to detect sounds) between the entity 106 and another entity, such as the entity 108, within a current context of the entity 106. The interaction monitor 148, in response to detecting interactions associated with the entity 106, may notify the processor 112 such that the processor 112 may facilitate collection of the plurality of data points 111 including audio data, image data, location data, and/or other data associated with entity 106. The interaction monitor 148 may distribute the data points 111 to the components 101a, 101b, where the components 101a may perform various analyses on the plurality of data points 111, and the components 101b may be configured to determine various decisions based on the plurality of data points 111, which will be further described below. In some examples, the components 101 may be controlled by the processor 112 of the device 110 to perform various operations based on the plurality of data points 111, where the data points 111 may be stored in the memory 114.

In some examples, the system 100 may be implemented with use of different devices, such as a mobile device, and components of a cloud computing environment (e.g., servers, processors, memory, and/or other components). In examples where the system 100 may be implemented on different devices, one or more components 101 of the system 100 may be located on one or more of the different devices. For example, components 101b and/or 101c may be parts of the device 110 while components 101a, instructions 116, and/or database 118 may be parts of a cloud computing environment. In some examples, placement of components 101 and/or database 118 may be based on an analysis of device capabilities (e.g., computation power, storage, security level, etc) of the device 110 and/or the components of the cloud computing environment.

In an example, the context analyzer 122 may be configured to determine a current context of the entity 106 and the entity 108 based on the plurality of data points 111. For example, the data points 111 may include first location data (e.g., global positioning system (GPS) coordinates) indicating a location of the entity 106 detected by the device 110, and may include second location data indicating a location of the entity 108 that may be sent from a different device (smart phone of the second entity) to the device 110. The context analyzer 122 may compare the first location with the second location data to determine a distance between the entity 106 and the entity 108. The context analyzer 122 may compare the distance with a distance threshold to determine whether the entity 106 and the entity 108 are separated. If the distance is greater than the threshold, then the context analyzer 122 may determine that the entity 106 is separated from the entity 108. The context analyzer 122 may also determine whether the entity 106 is in a specific location, such as a daycare, by searching for the first location data on a map application executable by the device 110, by using a proximity or crowd analysis. As such, the context analyzer 122 may determine a current context of the entity 106 and the entity 108 based on the determined location of the entity 106 and the distance in which the entity 106 is separated from the entity 108. In some examples, the context analyzer 122 may also search for known devices, such as a device associated with another entity (e.g., smart phone that belongs to the another entity) within a distance of the device 110 in order to determine a current context of the entity 106, such as identities of the entities surrounding the entity 106, and/or determine a number of entities surrounding the entity 106, such as by using a proximity analysis, crowd-density analysis or other mechanisms such as by communicating with nearby surveillance systems or devices that run computer vision and scene understanding algorithms.

In an example, the risk analyzer 124 may be configured to shape a system response of the system 100 in order to indicate which simulacrum may be appropriate for different levels, or degree, of separation anxiety being experienced by the entity 106. For example, if the entity 108 is separated from the entity 106 for ten minutes, the entity 106 may experience a relatively low degree of separation anxiety and a first simulacrum may be outputted the system 100, based on the shaped system response, in response to the relatively low degree of separation anxiety. However, if the entity 108 is away for a relatively long duration of time, such as three hours, the entity 106 may experience a relatively high degree of separation anxiety and a second simulacrum may be outputted by the system 100, based on the shaped system response, in response to the relatively high degree of separation anxiety. The risk analyzer 124 may be further configured to perform predictive analytics, such that the system 100 may anticipate behavior of the entity 106 and preemptively trigger an output of a simulacrum representative of an aspect of the entity 108 before a risk of separation anxiety reaches a threshold defined by the system 100. For example, the system 100 may monitor potential trigger of separation anxiety and output a simulacrum before the entity 106 experiencing separation anxiety.

In an example, the personality analyzer 126 may apply personality determination algorithms (which may be among the instructions 116) on the data points 111 to determine personalities of the first entity and the second entity. In another example, the personality analyzer 126 may analyze, based on the data points 111, how often the first entity laughs, cries, how loud the first entity talks, how quickly the first entity responds to commands from the second entity, and/or temperament of the first entity, in order to determine a personality of the first entity. The personality analyzer 126 may be activated upon an approval from the second entity, such that any information being collected, analyzed, and/or generated are subject to permission from the second entity or a guardian of the first entity. In some examples, any information and/or data collected, analyzed, generated, related to the first entity are processed by the system 100 in an anonymous manner in order to preserve privacy and protect the identity of the first entity.

In an example, the engagement analyzer 128 may apply algorithms among the instructions 116 on the data points 111 to determine engagement data between the first entity and the second entity. For example, the engagement analyzer 128 may determine that on one or more occasions, when the first entity cries, the second entity sings a particular song in response to the crying. In another example, the engagement analyzer 128 may determine that on one or more occasions, the first entity laughs in response to the second entity speaking a particular phrase. The engagement analyzer 128 may also record responses from the first entity in response to actions being performed by a second entity, such as, when the first entity stops crying in response to the second entity singing a particular song. The engagement analyzer 128 may also record reactions of the first entity in response to a second entity being away from the first entity. For example, the engagement analyzer 128 may detect whether the first entity cries after the second entity leaves the first entity, and how long the crying lasts. The engagement data generated by the engagement analyzer 128 may be stored in the memory 114, and may be distributed to other components 101, such as the decision engine 132, and/or the profiler engine 134. In some examples, the engagement data generated by the engagement analyzer 128 may be sent to the processor 112 such that the processor 112 may update the database 118 to include the engagement data.

In an example, the context analyzer 122 may notify the duration estimator 144 that the entity 106 is separated from the entity 108. The duration estimator 144 may start to determine a duration in which the entity 106 is separated, or predicted to be separated, from the entity 108. The duration estimator 144 may be configured to send the determined duration to other components 101 periodically, such as every five minutes, every half hour, and/or another amount of time.

The duration estimator 144 may send the determined duration to the context analyzer 122, where context analyzer 122 may perform analysis on the determined duration. For example, the context analyzer 122 may compare the determined duration with a duration threshold in response to the separation distance being greater than the distance threshold (described above). The context analyzer 122 may send the results of the comparisons to the separation anxiety detector 136.

In an example, the separation anxiety detector 136 may be configured to detect whether the entity 106 may be experiencing separation anxiety. The separation anxiety detector 136 may receive an indication from the context analyzer 122 that the entity 106 is separated, or predicted to be separated, from the entity 108. The separation anxiety detector 136 may also receive a duration in which the entity 106 is separated, or predicted to be separated, from the entity 108 from the duration estimator 144. The separation anxiety detector 136 may also receive results of the comparison between the separation duration with the duration threshold and the comparison between the separation distance with the distance threshold. In an example, if the separation duration is greater than the duration threshold and if the separation distance is greater than the distance threshold, the separation anxiety detector 136 may determine that the entity 106 may experience separation anxiety. In another example, if the separation duration is less than the duration threshold and if the separation distance is greater than the distance threshold, the separation anxiety detector 136 may use additional data (e.g., audio data described below) to determine whether the entity 106 may be experiencing separation anxiety.

The separation anxiety detector 136 may also receive audio data from the interaction monitor 148, where the received audio data may include an indication that the entity 106 is crying with corresponding timestamps. Based on the received indication of separation, duration of separation, and audio data, the separation anxiety detector 136 may determine whether separation anxiety is being experienced by the entity 106. Further, the separation anxiety detector 136 may determine whether separation anxiety is being experienced by the entity 106 based on a personality of the entity 106 determined by the personality analyzer 126. For example, if a first entity rarely cries, but started crying within a minute after being separated from a second entity, the separation anxiety detector 136 may determine that the first entity is experiencing separation anxiety. In another example, if a first entity tends to cry easily and started crying within a minute after being separated from the second entity, the separation anxiety detector 136 may determine that the first entity is not yet experiencing separation anxiety and may observe for a longer period of time before making a determination. In some examples, separation anxiety detector 136 may use the shaped system response outputted by the risk analyzer 124 to determine whether the entity 106 is experiencing separation anxiety. In addition, the separation anxiety detector 136 may determine whether separation anxiety is being experienced by a cohort of entities related, or similar, to entity 106 based on similarity of cohort entities personality analysis.

In an example, the profiler engine 134 may be configured to generate a profile for the first entity, the second entity (the entity 106 and the entity 108) and/or cohort of entities. For example, the profiler engine 134 may apply the instructions 116 on the data points 111 to determine a background, preferred communication language, and/or health issues and history associated with the first entity and the second entity. The profile engine 134 may generate a profile corresponding to both the first entity and the second entity, where the generated profile may be stored as part of the profile model 146 of the first entity, and in the memory 114. In some examples, the profile engine 134 may receive a personality or cohort of personalities determined by the personality analyzer 126 in order to generate a profile for the first entity based on the personality or cohort of personalities.

In addition to profiles and personality, the profile models 146 may include data and/or one or more custom trained machine learning models representative of behavior and reactions of a first entity in response to particular contexts. In some examples, profile models 146 may include one or more custom models trained by the processor 112 and/or the profile engine 134, such as by executing the one or more machine learning models among the instructions 116, based on the data points 111 and/or outputs generated by the one or more components 101. For example, an amount of separation time, or a predicted amount of separation time, between the second entity and the first entity may be used as training inputs, and an amount of crying time of the first entity in response to corresponding separation time, or a predicted amount of separation time, may be used as training labels, in order for the system 100 to learn a function and generate a model representative of the learned function. In some examples, outputs generated by the components 101 may be used by the processor 112 as weights to generate the profile models 146. For example, if a first entity cries relatively easily as indicated by outputs of the personality analyzer 126, the first entity may not be experiencing separation anxiety even if the first entity is crying after a relatively small amount of separation time from a second entity. As such, the personality of a first entity or cohort of personalities may be used as weights in the profile model 146 learned based on data associated with the first entity or cohort of entities. In some examples, the profile models 146 may be stored in the memory 114.

In some examples, the profile models 146 may be used by the separation anxiety detector 136 to detect whether the first entity is experiencing separation anxiety. For example, the profile models 146 may include historical data such as audio recordings of the first entity crying when experiencing separation anxiety. The separation anxiety detector 136 may compare audio data being collected by the interaction monitor 148 in the current context to historical audio data to determine whether the crying being recorded is a same type of cry indicated by the historical audio data. As such, the separation anxiety detector 136 may determine whether the first entity is experiencing separation anxiety based on the comparison.

In an example, the decision engine 132 may be configured to identify an aspect of the entity 108 that may alleviate separation anxiety being experienced by the entity 106, and identify an interaction device 102 that may be capable of outputting a simulacrum representative of the identified aspect. The decision engine 132 may receive a notification from the separation anxiety detector 136 indicating that the entity 106 is experiencing separation anxiety. In response to receiving the notification, the decision engine 132 may identify an aspect of the entity 108 from the database 118, where the database 118 may indicate that the identified aspect corresponds to a particular reaction that may be performed by the entity 106. For example, the database 118 may include data indicating that when a second entity sings a particular song, the first entity may stop crying. The decision engine 132 may identify the aspect of "singing the particular song" based on the correspondence to "stop crying" as indicated by the database 118.

The decision engine 132 may further identify one or more interaction devices 102 that may be configured to output a simulacrum representative of the identified aspect, such as, executing a playback of an audio recording where the second entity is singing the particular song. The decision engine 132 may determine that an interaction device such as a smart phone, smart speaker, may be capable of executing the playback, whereas a device such as a toy without a speaker, may be incapable of executing the playback. Further, the database 118 may include a list of interaction devices and associated functions (playback of sound, video, projections, movements) such that the decision engine 132 may identify one or more interaction devices capable of outputting simulacrums representative of the identified aspect based on the database 118.

In some examples, system 100 may generate the simulacrum 104 in response to identifying the aspect of the entity 108. For example, upon identifying that the entity 108 singing a song may reduce the level of separation anxiety being experienced by the first entity, processor 112 may retrieve an audio recording, which may have been stored in memory 114, to generate or transform an audio file represented in a format suitable to be played back by the identified interaction device. In another example, processor 112 may generate simulacrums including more than one aspect of the entity 108, such as, generating a multimedia file that may include one or more of, an image of the entity 108, a collection of images of the entity 108 or a set of entities related to entity 106, and/or an audio recording of the entity 108 singing a song.

In response to identifying the interaction device 102 to output a simulacrum, the processor 112 may generate the simulacrum configuration 142, where the simulacrum configuration 142 may include data associated with configurations of one or more simulacrums, or the processor 112 may fetch data from a remote data store using metadata of the identified simulacrum. For example, as mentioned above, the system 100 may be configured prior to an implementation of the system 100 in order to control the simulacrum that may be outputted. Configurations of simulacrums may include a degree of realism of each simulacrum representative of an image, or a collection of images, of a second entity or a set of entities related to the first entity. In an example, prior to implementation of the system 100, a voice of a second entity may be recorded and the second entity may review the recording for approval, where the approved recording may be stored as a part of the simulacrum configurations 142 for future use in selection or generation of simulacrums by the system 100.

In an example, instead of having the decision engine 132 identifying an aspect, the content item selector 138 may identify content, such as videos, songs, images, available on the Internet, which may alleviate separation anxiety being experienced by the entity 106. For example, the profile model 146 may indicate that the first entity likes a particular nursery rhyme, and the content item selector 138 may retrieve a sound file, or a video, or a link to a video that include the particular nursery rhyme. The decision engine 132 may identify an interaction device 102 that may output the identified content. For example, the decision engine 132 may determine that a tablet computer, or a smart phone, may include a browser or mobile application to output a video, while a smart speaker, or an interactive toy, may not be capable of outputting a video.

In an example, the decision engine 132 may further identify an aspect of the entity 108 based on a degree of separation anxiety being experienced by the entity 106. The risk analyzer 124, as described above, may shape a response of the system 100, and the decision engine 132 may identify an aspect of the entity 108 based on the shaped response of the system 100. For example, the duration estimator 144 may track how long the first entity has been crying, or predicted/estimated crying duration, and audio data collected by the interaction monitor 148 may indicate a volume, intensity, amplitude, of the crying noise produced by the first entity. Based on the duration and the audio data, the separation anxiety detector 136 may determine a degree of separation anxiety. The degree of separation anxiety may include numerical values, text, and/or other representations. For example, the degree of separation anxiety may range from "1" to "5", where a degree of "5" may be a highest degree. The decision engine 132 may compare the degree of separation anxiety with a threshold, which may be indicated in the instruction 116, in order to identify an aspect that may alleviate the separation anxiety being experienced by the entity 106. For example, the decision engine 132 may identify, such as by analyzing the database 118, that a second entity singing a particular song may alleviate separation anxiety of a degree "2" and an image of a second entity may alleviate separation anxiety of a degree "3". As such, the decision engine 132 may identify an aspect of the entity 108 to effectively alleviate separation anxiety being experienced by the entity 106. Further, the predicted amount separation duration (e.g., predicted crying duration) may be used by the decision engine 132 in order to determine and identify at least one effective aspect of the entity 108 in advance (e.g., prior to the entity 106 experiencing separation anxiety).

During an output of the simulacrum 104, the interaction monitor 148 may continue to monitor an interaction between the entity 106 and the outputted simulacrum 104. The interaction monitor 148 may continue to collect plurality of data (e.g., audio, image, and/or other external contextual data such as environmental situations like ambient noise level, lighting condition, crowd-density, etc.), which may indicate how the entity 106 reacts to the outputted simulacrum and how the external contextual data has impacted (positively or negatively) the outputted simulacrum. In an example, based on the newly collected data (e.g., audio), the separation anxiety detector 136 may determine an updated degree of separation anxiety being experienced by the entity 106. If the degree of separation anxiety has increased, the separation anxiety detector 136 may notify the decision engine 132, and the decision engine 132 may identify another aspect of the entity 108 that may alleviate, or reduce, the degree of separation anxiety. If the degree of separation anxiety has decreased, the system 100 may continue to output the same simulacrum 104 until the separation anxiety detector 136 detects that the entity 106 is no longer experiencing separation anxiety. Further, audio data collected during interaction of the entity 106 with the simulacrum 104 may be used by the components 101 to update various historical data, models, profiles, associated with the entity 106. For example, a particular aspect of the entity 108 may alleviate separation anxiety experienced by the entity 106 two weeks ago, but may no longer be effective—such changes may be updated by the processor 112 or the components 101 by updating any historical data, models, and profiles associated with the entity 106.

The context analyzer 122 may determine the impact of the external contextual data by analyzing and triangulating with the outputted simulacrum in relation to separation anxiety experience. The analysis of the collected external contextual data may be stored for future use by the system 100 in order to optimize the entity 106 interaction and separation anxiety experience.

In some examples, the context analyzer 122 may also determine an anticipated separation time between the entity 106 and the entity 108. For example, if the first entity typically goes to daycare for a number of hours on every weekday, the context analyzer 122 may determine a current date and time in order to determine a remaining separation time in which the entity 106 will be separated from entity 108. The decision engine 132 may identify aspects of the entity 108 based on the anticipated or predicted separation time.

The interface manager 150 may be configured to monitor a user interface that may be displayed on a screen of the device 110. The user interface may present options for a user of the device 110 to start and/or end execution of the system 100, to select simulacrums to be outputted, to confirm various actions such as output of a simulacrum, outputting a simulacrum by particular device, and/or other actions. For example, the device 110 may be a smart phone, or a tablet computer, controlled by a caregiver in a daycare. When a first entity is experiencing separation anxiety, the caregiver may control the device 110 to implement the system 100 in order to configure, or trigger, one or more interaction devices 102 to output the simulacrum to alleviate the separation anxiety being experienced by the first entity.

Figure 2:
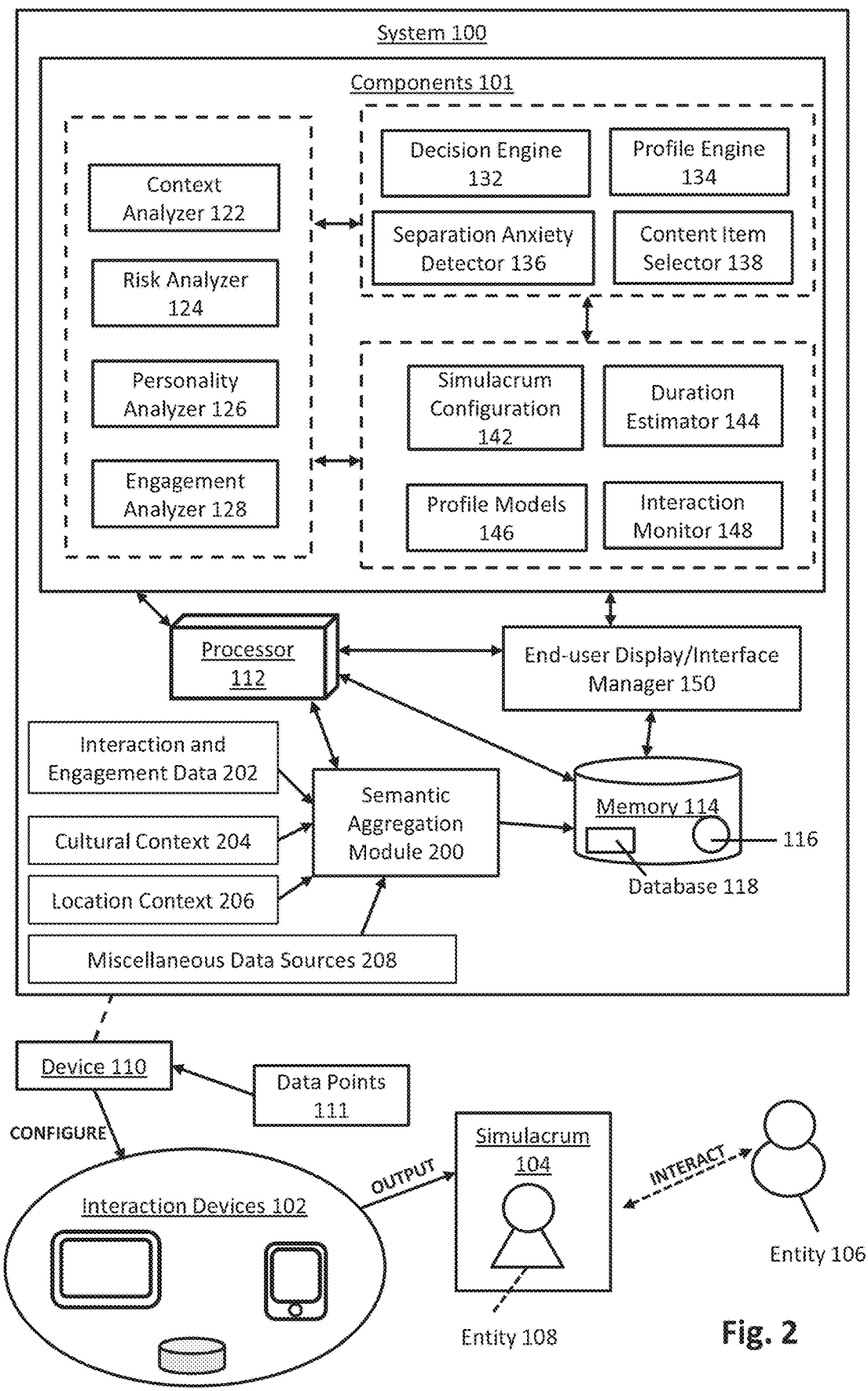
FIG. 2 illustrates the example system of FIG. 1 with additional details relating to simulacrum generation based on separation anxiety in one embodiment.

FIG. 2 illustrates the example system of FIG. 1 with additional details relating to simulacrum generation based on separation anxiety, arranged in accordance with at least some embodiments described herein. FIG. 2 is substantially similar to computer system 100 of FIG. 1, with additional details. Those components in FIG. 2 that are labeled identically to components of FIG. 1 function as described with reference to FIG. 1.

As shown in an example in FIG. 2, the system 100 may further include a semantic aggregation module 200. In some examples, the semantic aggregation module 200 may be a component among components 101. The semantic aggregation module 200 may be configured to be in communication with the processor 112, the components 101, the interface manager 150, and/or the memory 114. The semantic aggregation module 200 may be configured to aggregate and/or transform the data points 111, and outputs generated from the components 101, into contents of the database 118. In the example shown in FIG. 2, the semantic aggregation module 200 may receive interaction and engagement data 202 that may include interaction data collected by the interaction monitor 148 and engagement data generated by the engagement analyzer 128. The interaction and engagement data 202 may include data associated with historical behavioral data, historical interactions of the first entity with other entities.

The semantic aggregation module 200 may further receive the cultural context 204 from the profile engine 134 and/or context analyzer. The cultural context 204 may include a profile and/or background of the first entity. The semantic aggregation module 200 may further receive location context 206 from the context analyzer 122. The location context 206 may include indications of a current location of the entity 106, current location of the entity 108, historical locations of the entity 106, historical locations of the entity 108, and/or locations (e.g., daycare) that may be flagged by a user of the system 100. The semantic aggregation module 200 may further receive miscellaneous data sources 208 from other components 101, or from contexts outside of the device 110, such as external contextual data such as environmental situations like ambient noise level, lighting condition, crowd-density, etc. For example, the miscellaneous data sources 208 may include data from computing devices or sensors such as smart watch, mobile device, history of concerns/risk, and/or historical calendar data.

The semantic aggregation module 200 may aggregate the interaction and engagement data 202, the cultural context 204, the location context 206, the miscellaneous data sources 208, and/or the data points 111. For example, the semantic aggregation module 200 may apply a portion of the instructions 116 on the interaction and engagement data 202 in order to link particular actions of a second entity to particular reactions from the first entity. In an example, the interaction and engagement data 202 may indicate that the first entity laughs in response to the second entity speaking a particular phrase. The semantic aggregation module 200 may link the reaction of "laugh" to the particular phrase, and may update the database 118 to indicate the link. In another example, the semantic aggregation module 200 may derive data that may be stored in the database 118. For example, the semantic aggregation module 200 may apply noise recognition algorithms, light intensity analysis, crowd-density algorithms, among the instructions 116 to derive classification data from audio data, such as deriving a recording of a second entity singing into a piece of data labeled as a particular aspect of the second entity, or deriving a recording of a first entity crying into a piece of data associated with a negative emotion.

A system in accordance with the present disclosure may output a suitable list of content pertaining to reduction of separation anxiety being experienced by a first entity, where the suitable list of content may include predefined or tailored content based on a type and a degree separation anxiety being experienced by the first entity. A system in accordance with the present disclosure may provide virtual reality and simulacrums in interactive communication systems directed to improvements in reducing separation anxiety being experienced by the first entity when the first entity is separated from a second entity, or a group of entities related to the first entity. The system in accordance with the present disclosure may provide improvements in various "doll therapy," that utilizes interactive communication systems, particularly in geropsychiatric and dementia care settings, being used to aid the first entity who may experience separation anxiety when separated from the second entity. The system in accordance with the present disclosure may also provide clinical benefits in the care of patients with dementia and mental health treatments that uses interactive communication systems. The system in accordance with the present disclosure may also provide a practical application to address challenges of having a time-limited intervention in treatments of psychiatric disorders which may use interactive communication systems. Further, by utilizing a device to implement the system in accordance with the present disclosure to configure a plurality of interaction devices, the system may be deployed and implemented in various locations without the burden of moving a plurality of devices with the first entity. For example, when a first entity goes to a daycare, a user or another in the daycare may implement the system in accordance with the present disclosure to configure interaction devices that may already be located within the daycare, without a need for a second entity to bring items that may reduce separation anxiety that may be experienced by the first entity.

Figure 3:
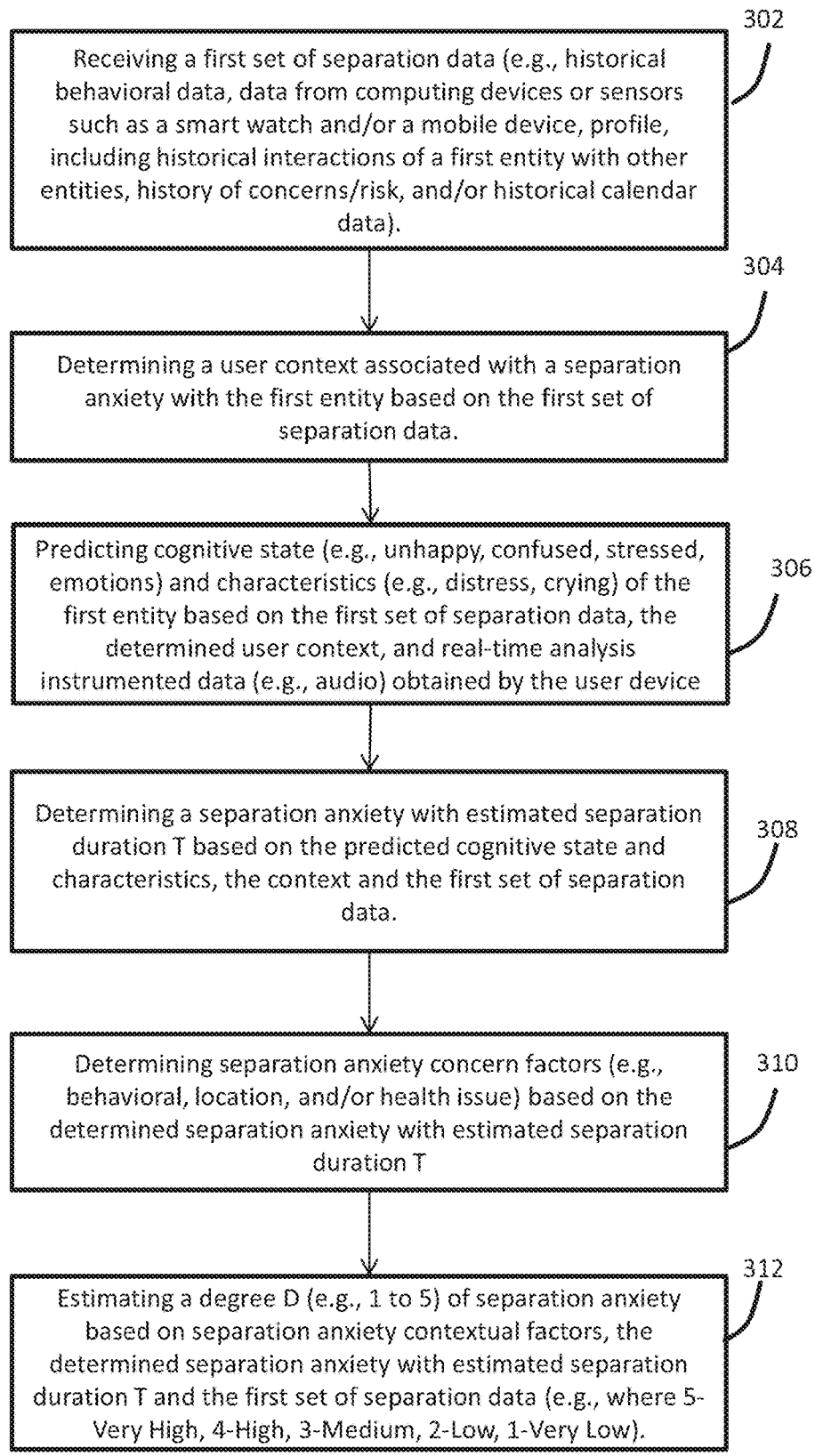
FIG. 3 illustrates a flow diagram of a process relating to determination of a degree of separation anxiety in one embodiment.

FIG. 3 illustrates a flow diagram relating to determination of a degree of separation anxiety, arranged in accordance with at least some embodiments presented herein. The process in FIG. 3 may be implemented using, for example, computer system 100 discussed above. An example process may include one or more operations, actions, or functions as illustrated by one or more of blocks 302, 304, 306, 308, 310, and/or 312. Although illustrated as discrete blocks, various blocks may be divided into additional blocks, combined into fewer blocks, eliminated, or performed in parallel, depending on the desired implementation.

Processing may begin at block 302, where the processor 112 of the device 110 (as shown in FIG. 1 and FIG. 2, and described above) may receive separation data that may include historical behavioral data, data from computing devices or sensors such as a smart watch and/or a mobile device, a profile including historical interactions of the first entity with other entities, history of concerns/risk, background of the first entity, and/or historical calendar data. The processor 112 may retrieve the separation data from the memory 114. The separation data may include the data points 111 and outputs generated by the components 101 shown in FIG. 1 and FIG. 2, and described above.

Processing may continue from block 302 to block 304. At block 304, the processor 112 may determine a user context associated with a separation anxiety with a first entity based on the first set of separation data. For example, the processor 112 may determine a current context indicating whether the first entity is separated from the second entity, a duration in which the first entity is separated from the second entity, a current location of the first entity and the second entity, a number of entities within a vicinity of the first entity, and/or other information.

Processing may continue from block 304 to block 306. At block 306, the processor 112 of the device 110 may predict a cognitive state of the entity 106, such as unhappy, confused, stressed, emotions, and may identify a set of characteristics (e.g., distress, crying) based on various real-time analysis data (e.g., audio) captured by the instruction monitor 148, and based on the separation data. In some examples, the interaction monitor 148 (shown in FIG. 1 and FIG. 2, and described above) may collect various data (e.g., audio) from the entity 106, and the semantic aggregation module 200 (shown in FIG. 2 and described above), and may classify the audio data as one or more cognitive states. The processor 112 may predict the cognitive state of a first entity based on the data aggregated by the semantic aggregation module 200, which may be stored in the memory 114 of the device 110 as content of the database 118.

Processing may continue from block 306 to block 308. At block 308, the processor 112 of the device 110 may determine a separation anxiety with an estimated separation duration "T" based on the predicted cognitive state and characteristics of the first entity, the context of the second entity, and the first set of separation data.

Processing may continue from block 308 to block 310. At block 310, the processor 112 of the device 110 may determine separation anxiety concern factors (e.g., behavioral, location, health issue) based on the determined separation anxiety with estimated separation duration T.

Processing may continue from block 310 to block 312. At block 312, the processor 112 of the device 110 may estimate a degree "D", which may range from "1" to "5", of separation anxiety based on separation anxiety contextual factors, the determined separation anxiety with estimated separation duration "T" and the first set of separation data.

Figure 4:
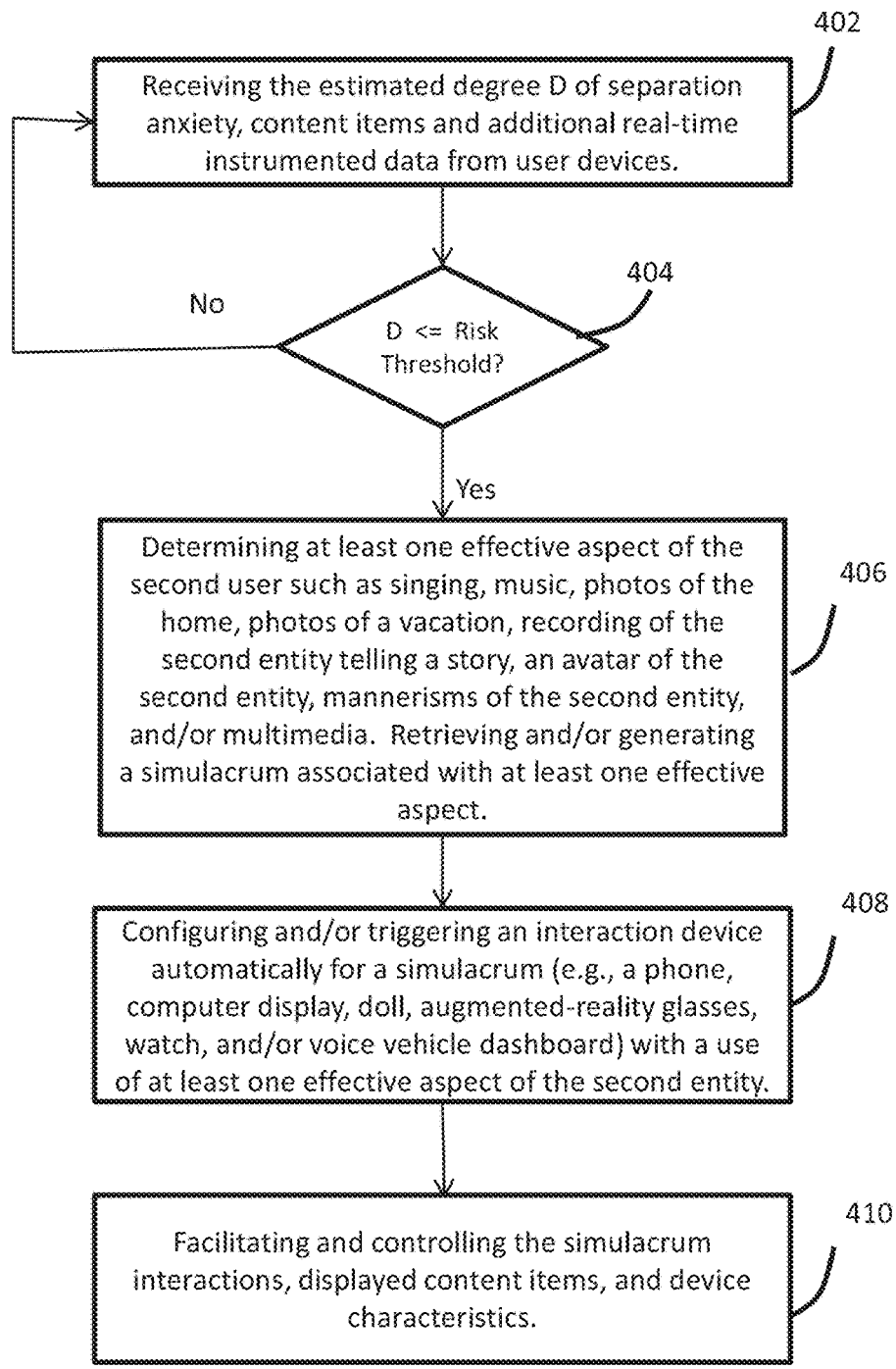
FIG. 4 illustrates a flow diagram relating to an output of a simulacrum in one embodiment.

FIG. 4 illustrates a flow diagram relating to an output of a simulacrum, arranged in accordance with at least some embodiments presented herein. The process in FIG. 4 may be implemented using, for example, computer system 100 discussed above. An example process may include one or more operations, actions, or functions as illustrated by one or more of blocks 402, 404, 406, 408, and/or 410. Although illustrated as discrete blocks, various blocks may be divided into additional blocks, combined into fewer blocks, eliminated, or performed in parallel, depending on the desired implementation.

Processing may begin at block 402, where the processor 112 of the device 110 may receive degree of separation anxiety "D". The processor 112 may further receive content items, such as videos fetched from online video streaming services, for effective simulacrum output. The processor 112 may further analyze real-time instrumented data (e.g., audio) collected by the interaction monitor 148, and further analyze the fetched content items to determine one or more effective simulacrum outputs.

Processing may continue from block 402 to block 404. At block 404, the processor 112 may compare the degree of separation anxiety "D" with a risk threshold. The processor 112, based on the comparison of the degree of separation anxiety "D" with the risk threshold, may determine whether the degree of separation anxiety "D" is greater than or equal to the risk threshold. In some examples, the decision engine 132 or the separation anxiety detector 136 may perform the comparison of the degree of separation anxiety "D" with the risk threshold. If the degree of separation anxiety "D" is less than the risk threshold, the process may return to block 402 in order for the processor 112 to receive another degree of separation anxiety at a subsequent time instance.

Processing may continue from block 404 to block 406. At block 406, in response to the degree of separation anxiety "D" being greater than or equal to the risk threshold, the processor 112 may determine at least one effective aspect of the entity 108, such as second entity singing, music, photos of the home, photos of a vacation, recording of second entity telling a story, an avatar of the second entity, mannerisms of second entity, and/or multimedia. The processor 112 may generate a simulacrum associated with the determined aspect of the entity 108.

Processing may continue from block 406 to block 408. At block 408, the processor 112 may configure an interaction device 102 automatically (e.g., a phone, computer display, doll, augmented-reality glasses, watch, voice vehicle dashboard, and/or another interaction device) to output a simulacrum representing an aspect of the second entity.

Processing may continue from block 408 to block 410. At block 410, the processor 112 may facilitate and/or control the outputted simulacrum interactions, displayed content items, and device characteristics.

Figure 5:
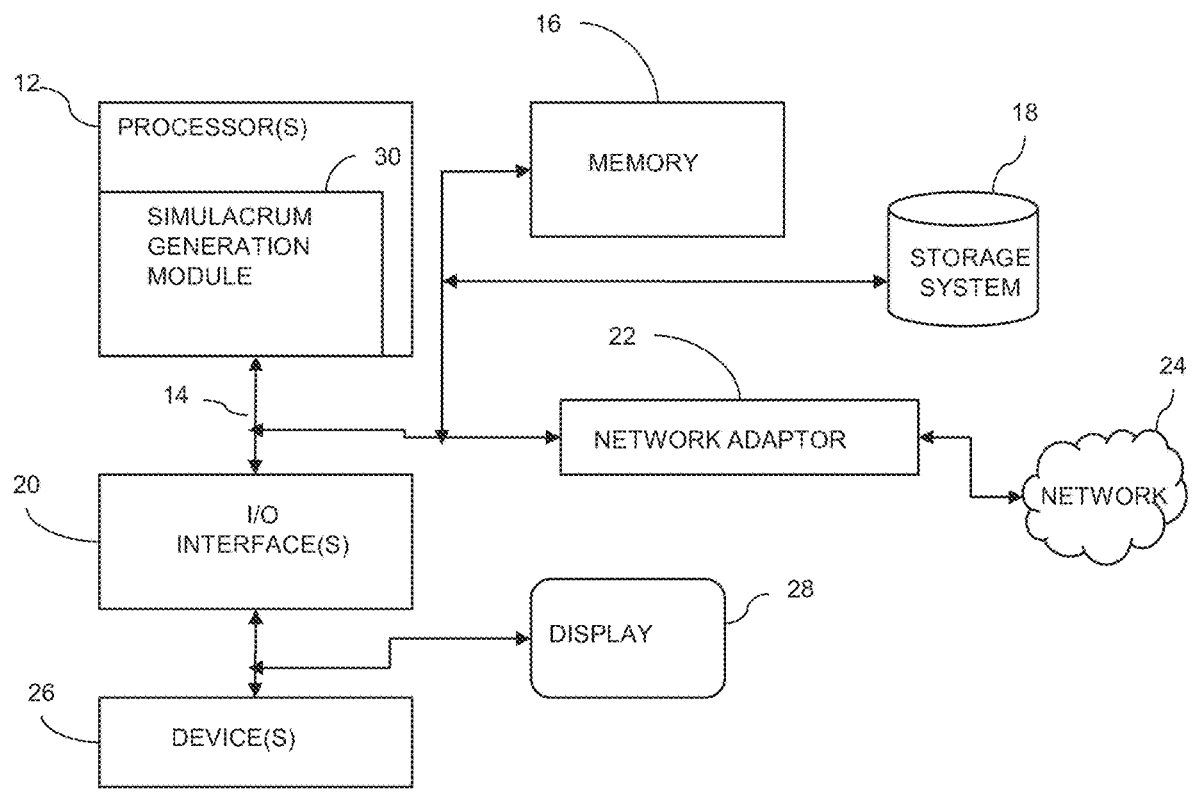
FIG. 5 illustrates a schematic of an example computer or processing system that may implement simulacrum generation based on separation anxiety in one embodiment of the present disclosure.

FIG. 5 illustrates a schematic of an example computer or processing system that may implement simulacrum generation based on separation anxiety in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 4 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, supercomputers, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 (e.g., simulacrum generation module 30) that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 6:
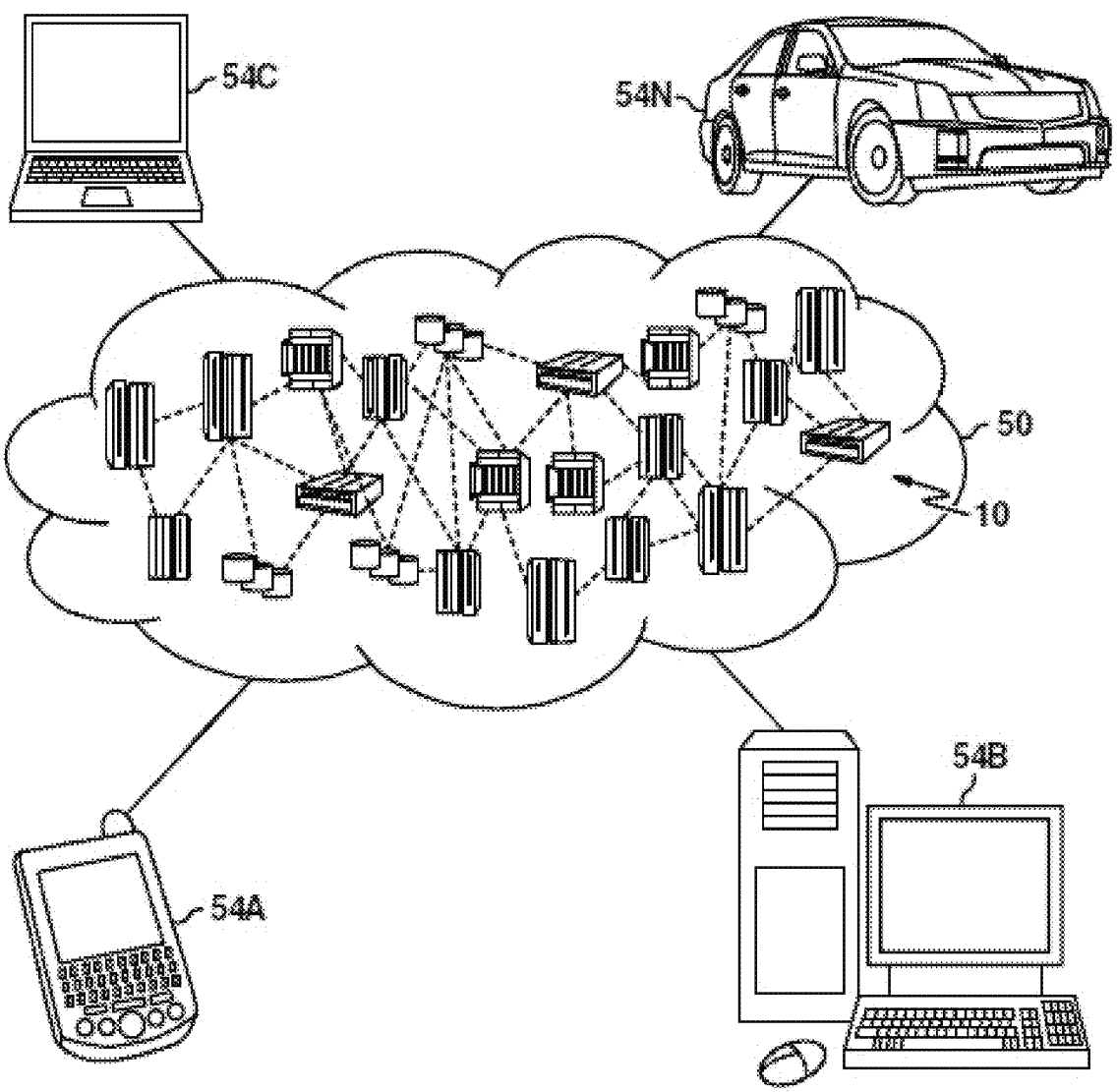
FIG. 6 depicts a cloud computing environment according to an embodiment of the present invention.

FIG. 6 depicts a cloud computing environment according to an embodiment of the present invention. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 7:
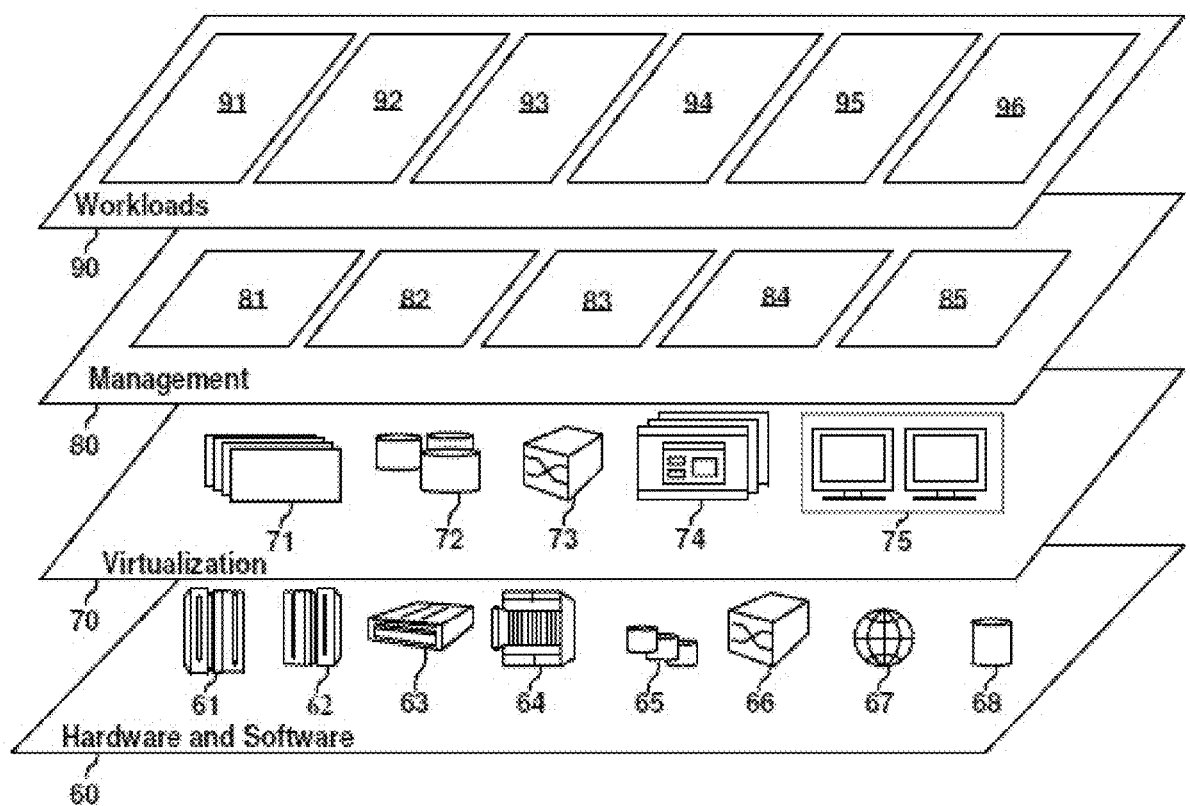
FIG. 7 depicts abstraction model layers according to an embodiment of the present invention.

FIG. 7 depicts abstraction model layers according to an embodiment of the present invention. Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and simulacrum generation 96.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for generating a simulacrum representative of an entity, the method comprising:
   training, by a computer device, a machine learning model using engagement data associated with historical interactions between a first entity and a plurality of entities;
   running, by the computer device, the trained machine learning model to derive classification data indicating at least one reaction of the first entity to a plurality of aspects of the plurality of entities;
   storing, by the computer device, the classification data in a database stored in a memory;
   determining, by the computer device, a current context associated with the first entity and a second entity, wherein the second entity is among the plurality of entities, and the current context indicates that the first entity and the second entity are separated;
   detecting, by the computer device, that the first entity is experiencing a behavior relating to the separation of the first entity and the second entity;
   in response to detecting that the first entity is experiencing the behavior, performing, by the computer device, a lookup function in the database stored in the memory to identify an aspect of the second entity corresponding to a particular reaction by the first entity;
   identifying, by the computer device, an interaction device that is capable of outputting a simulacrum representative of the identified aspect of the second entity; and
   triggering, by the computer device, the identified interaction device to output the identified simulacrum.

2. The method of claim 1, wherein determining the current context includes:
   determining, by the computer device, a first location of the first entity and a second location of the second entity;
   determining, by the computer device, a distance between the first location and the second location;
   determining, by the computer device, that the distance is greater than a distance threshold; and
   in response to the distance being greater than the threshold, determining, by the computer device, that the first entity is separated by the second entity.

3. The method of claim 1, wherein determining the current context includes determining a duration in which the first entity and second entity are separated.

4. The method of claim 3, wherein detecting that the first entity is experiencing the behavior is based on the duration in which the first entity and second entity are separated.

5. The method of claim 1, wherein detecting that the first entity is experiencing the behavior includes:
   determining, by the computer device, a degree of the behavior based on the current context;
   comparing, by the computer device, the degree of the behavior with a threshold; and
   in response to the degree of the behavior being greater than the threshold, determining that the first entity is experiencing the behavior.

6. The method of claim 1, wherein the aspect is a first aspect of the second entity, detecting that the first entity is experiencing the behavior includes determining, by the computer device, a first degree of the behavior based on the current context, and subsequent to the output of the simulacrum, the method further comprising:
   determining, by the computer device, a second degree of the behavior being experienced by the first entity in response to the output of the simulacrum;
   comparing, by the computer device, the first degree of the behavior with the second degree of behavior;
   in response to the second degree of the behavior being greater than the first degree of the behavior, identifying, by the computer device, a second aspect of the second entity;
   triggering, by the computer device, the identified interaction device to output a new simulacrum representative of the second aspect of the second entity.

7. The method of claim 1, further comprising:
   collecting responses from the first entity to the outputted simulacrum; and
   updating the engagement data based on the collected responses.

8. The method of claim 1, further comprising generating, by the computer device, the simulacrum prior to triggering the identified interaction device to output the simulacrum.

9. A system effective to generate a simulacrum representative of an entity, the system comprising:
   a memory configured to store a set of instructions;
   a processor configured to be in communication with the memory;
   at least one interaction device configured to be in communication with the processor;
   the processor being configured to execute the set of instructions to:
      train a machine learning model using engagement data associated with historical interactions between a first entity and a plurality of entities;
      run the trained machine learning model to derive classification data indicating at least one reaction of the first entity to a plurality of aspects of the plurality of entities;
      store the classification data in a database stored in the memory;
      determine a current context associated with the first entity and a second entity, wherein the second entity is among the plurality of entities, and the current context indicates that the first entity and second entity are separated;
      detect that the first entity is experiencing a behavior relating to the separation of the first entity and the second entity;
      in response to the detection that the first entity is experiencing the behavior, perform a lookup function in the database stored in the memory to identify an aspect of the second entity corresponding to a particular reaction by the first entity;
      identify an interaction device among the at least one interaction device, wherein the identified interaction device is capable of outputting a simulacrum representative of the identified aspect of the second entity; and trigger the identified interaction device to output the identified simulacrum.

10. The system of claim 9, wherein the processor is further configured to execute the set of instructions to:
determine a first location of the first entity and a second location of the second entity;
determine a distance between the first location and the second location;
determine that the distance is greater than a distance threshold; and
in response to the distance being greater than the threshold, determine that the first entity is separated by the second entity.

11. The system of claim 9, wherein the processor is further configured to execute the set of instructions to determine a duration in which the first entity and second entity are separated.

12. The system of claim 11, wherein the detection that the first entity is experiencing the behavior is based on the duration in which the first entity and second entity are separated.

13. The system of claim 9, wherein the processor is further configured to execute the set of instructions to
determine a degree of the behavior based on the current context;
compare the degree of the behavior with a threshold; and
in response to the degree of the behavior being greater than the threshold, determine that the first entity is experiencing the behavior.

14. The system of claim 9, wherein the aspect is a first aspect of the second entity, and the processor is further configured to execute the set of instructions to:
determine a first degree of the behavior based on the current context, and subsequent to the output of the simulacrum, the method further comprising:
determine a second degree of the behavior being experienced by the first entity in response to the output of the simulacrum;
compare the first degree of the behavior with the second degree of the behavior;
in response to the second degree of the behavior being greater than the first degree of the behavior, identify a second aspect of the second entity;
trigger the identified interaction device to output a new simulacrum representative of the second aspect of the second entity.

15. The system of claim 9, wherein the processor is further configured to execute the set of instructions to:
collect responses from the first entity to the outputted simulacrum; and
update the engagement data based on the collected responses.

16. The system of claim 9, wherein the processor is further configured to generate the simulacrum prior to the trigger of the identified interaction device to output the simulacrum.

17. A computer program product for generating a simulacrum representative of an entity, the computer program product comprising a computer readable storage medium having program instructions embodied therewith, the program instructions executable by a processing element of a device to cause the device to:
train a machine learning model using engagement data associated with historical interactions between a first entity and a plurality of entities;
run the trained machine learning model to derive classification data indicating at least one reaction of the first entity to a plurality of aspects of the plurality of entities;
store the classification data in a database stored in a memory;
determine a current context associated with first entity and a second entity, wherein the second entity is among the plurality of entities, and the current context indicates that the first entity and second entity are separated;
detect that the first entity is experiencing a behavior relating to the separation of the first entity and the second entity;
in response to detecting that the first entity is experiencing the behavior, perform a lookup function in the database stored in the memory to identify an aspect of the second entity corresponding to a particular reaction by the first entity;
identify an interaction device that is capable of outputting a simulacrum representative of the identified aspect of the second entity; and
trigger the identified interaction device to output the identified simulacrum.

18. The computer program product of claim 17, wherein the program instructions are further executable by the processing element of a device to cause the device to:
determine a first location of the first entity and a second location of the second entity;
determine a distance between the first location and the second location;
determine that the distance is greater than a distance threshold; and
in response to the distance being greater than the threshold, determine that the first entity is separated by the second entity.

19. The computer program product of claim 17, wherein the program instructions are further executable by the processing element of a device to cause the device to determine a duration in which the first entity and second entity are separated, and wherein the detection that the first entity is experiencing the behavior is based on the duration in which the first entity and second entity are separated.

20. The computer program product of claim 17, wherein the aspect is a first aspect of the second entity, and the program instructions are further executable by the processing element of a device to cause the device to:
determine a first degree of the behavior based on the current context, and subsequent to the output of the simulacrum, the method further comprising:
determine a second degree of the behavior being experienced by the first entity in response to the output of the simulacrum;
compare the first degree of the behavior with the second degree of the behavior;
in response to the second degree of behavior being greater than the first degree of the behavior, identify a second aspect of the second entity;
trigger the identified interaction device to output a new simulacrum representative of the second aspect of the second entity.

* * * * *